United States Patent [19]
Yamagata et al.

[11] Patent Number: 5,665,570
[45] Date of Patent: Sep. 9, 1997

[54] ANTIBODY-ENCODING RECOMBINANT DNA AND ITS USE

[75] Inventors: Hideo Yamagata, Hachioji; Shigezo Udaka, Nagoya; Yasushi Inoue, Funahashi; Hiroko Tada, Okayama; Susumu Iwasa, Tsuzuki-gun, all of Japan

[73] Assignee: Takeda Chemical Industries, Ltd., Osaka, Japan

[21] Appl. No.: 384,545

[22] Filed: Feb. 7, 1995

[30] Foreign Application Priority Data

Feb. 10, 1994 [JP] Japan ............... 6-016385

[51] Int. Cl.$^6$ .............. C12P 21/08; C12N 1/20; C12N 15/75; C07H 21/04
[52] U.S. Cl. .............. 435/69.6; 435/69.1; 435/252.3; 435/320.1; 536/23.1
[58] Field of Search .............. 435/69.1, 71.2, 435/172.3, 320.1, 833; 536/23.1, 23.53; 935/23, 24, 29, 41; 530/387.3

[56] References Cited

U.S. PATENT DOCUMENTS 4,946,778  8/1990  Ladner et al. ............... 435/69.7

FOREIGN PATENT DOCUMENTS

| 0 146 901 | 7/1985 | European Pat. Off. . |
| 0 491 351 A2 | 6/1992 | European Pat. Off. . |
| 0614982A1 | 9/1994 | European Pat. Off. . |
| 0 614 982 A1 | 9/1994 | European Pat. Off. . |

OTHER PUBLICATIONS

Wu et al. (1993) Bio/Techology 11:71–76 Jan. 1993.
Konishi et al. (1990) Appl. Microbiol. Biotechnol. 34:297–302.
Yamagata et al. (1989) Proc. Natl. Acad. Sci. USA 86:3589–3593 May 1989.
Udaka and Yamagata (1993) Meth. Enzymol. 217:23–33.
H. Yamagata et al., *Agricultural and Biological Chemistry*, 48(4):1069–1071 (1984).
H. Takagi et al., *Agricultural and Biological Chemistry*, 53(8):2279–2280 (1989).
H. Yamagata et al., *Proceedings of the National Academy of the USA*, 86(10):3589–3593 (1989).
S. Udaka et al., *Methods in Enzymology*, 217:23–33 (1993).
Derwent Abstract of Japanese Published Unexamined Patent Application (Kokai tokkyo koho) No. 6–296485.
H. Tada et al., *Journal of Biotechnology*, 33:157–174 (1994).

Primary Examiner—David Guzo
Assistant Examiner—Robert Schwartzman
Attorney, Agent, or Firm—David G. Conlin; Peter F. Corless; Cara Z. Lowen

[57] ABSTRACT

A bacterium of the genus Bacillus is transformed by introducing a vector incorporating DNA encoding an antibody; the resulting transformant is cultivated in a medium to produce and accumulate the antibody in an active form in the culture liquid. According to this method, a recombinant antibody can be easily produced in an active form in large amounts, owing to success in secretory expression using a bacterium of the genus Bacillus.

17 Claims, 4 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:1:

CTCCCATGGC TTTCGCTGAT ATTCAGCTGA CACAGTC          37

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:2:

AAACTCGAGC TAACACTCTC CGCGGTTGA          29

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:3:

CTCCCATGGC TTTCGCTGAG GTGCAACTAG TGGAGTC          37

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: Other nucleic acid     ( x i ) SEQUENCE DESCRIPTION: SEQ ID NO:4:

AAAAAGCTTT CACGGTGGAC ACGTGTGAGT TT          32

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single -continued (D) TOPOLOGY: linear (ii) MOLECULE TYPE: Other nucleic acid (xi) SEQUENCE DESCRIPTION: SEQ ID NO:5:

AAACTCGAGA GAGGAGGAGA ACACAAGGT 29

ANTIBODY-ENCODING RECOMBINANT DNA AND ITS USE

FIELD OF THE INVENTION

The present invention relates to a recombinant DNA technology for antibody production. More specifically, the present invention relates to a DNA containing an antibody gene, a bacterium of the genus Bacillus carrying said DNA, and a method of producing an antibody using them. The antibody of the present invention is used as a therapeutic drug or diagnostic reagent for various diseases.

BACKGROUND OF THE INVENTION

Since the 1975 report by Köhler and Milstein regarding cell fusion technology [Nature, 256, 495 (1975)], the monoclonal antibody has been very useful in various fields, including basic research into cell physiology and immunology, detection, quantification, separation and purification of biological trace components, and diagnosis and treatment of various diseases. Thanks to advances in gene recombination technology, diagnostically or therapeutically more useful antibodies, such as mouse/human chimeric antibodies, humanized antibodies, single-chain antibodies, bispecific antibodies and toxin fusion antibodies have recently been prepared [Encyclopedia of Human Biology, 5, 81 (1991)]. Mouse/human chimeric antibodies and humanized antibodies, in particular, are advantageous for human administration, because the constant region and/or frame region of the mouse antibody, which is responsible for most immunogenicity, is of the human type [Nature, 314, 268 (1985); Nature, 321, 522 (1986)].

In expressing such recombinant antibodies, animal cells, especially mouse myeloma cells and CHO cells, are normally used. However, the use of these cells is economically problematic due to some drawbacks, such as expensive culture medium and long cultivating time. Also, since the degree of recombinant protein expression in animal cells is very low, various attempts have been made to achieve high expression. However, large amounts of medium must be used to obtain practically sufficient amounts of antibody, or cultivating time has to be extended much more with application of feed [Bio/Technology, 10, 169 (1992)], because the amount of protein expressed per unit volume of medium is generally low. Another drawback resides in the process for isolating the desired antibody; a great deal of time and labor is required to purify the protein from the culture broth. As for antibody expression in *Escherichia coli*, which is expected to offer high expression, many attempts have been reported, but most have failed to achieve practically acceptable levels of expression. The reasons for this situation include the following: 1) It is very difficult to express the entire IgG antibody molecule in *Escherichia coli*, due to complex conformation, especially S-S crosslinkages. 2) Although high expression has been achieved for antibodies of low molecular weight, such as functional antigen binding fragments Fv, Fab and Fab' [Science, 240, 1038 (1988); Nature, 347, 497 (1990); Bio/Technology, 10, 163 (1992)], single-chain antibodies (scAb) [Science, 242, 423 (1988)] and single-domain antibodies (dAb) [Nature,, 341, 544 (1989)], inactive inclusion bodies often form; active forms have rarely been recovered in sufficient amounts. 3) In *Escherichia coli*, the expressed antibody accumulates intracellularly in insoluble form, its purification taking vast amounts of time and labor, since the desired antibody must be isolated from the mixture of proteins derived from *Escherichia coli* after disruption of the cells of *Escherichia coli*. Furthermore, the desired antibody is liable to be decomposed by proteases derived from the host, *Escherichia coli*, during the complicated process. In short, it is difficult to produce an antibody in active form at high purity in large amounts by conventional methods.

As stated above, when a gene product of complex conformation from a higher organism is produced in a bacterial host-vector system such as *Escherichia coli*, it often accumulates in cells in the form of an inactive inclusion body [Journal of Biotechnology, 1, 307 (1984)] or undergoes decomposition [Gene, 34, 1 (1985)]; recovery is difficult while bioactivity is maintained.

The importance of recombinant antibodies, which are expected to exhibit various bioactivities, has steadily increased in the fields of diagnosis and treatment; there is strong need for a method of producing an antibody in an active form at low cost in large amounts.

Some bacteria of the genus Bacillus are known to produce certain extracellular protein; for example, *Bacillus brevis* is reported as possessing such function [Methods in Enzymology, 217, 23 (1993)]. By testing such *Bacillus brevis* bacteria for high production of proteins and no or little extracellular secretion of proteases, several strains have been selected and cloned with prominent characteristics. For example, Udaka [Agric. Biol. Chem., 40, 523(1976)] and Takagi [Agric. Biol. Chem.., 53, 691(1989)] established the strains of *Bacillus brevis* 47 and HPD31, respectively. Using these strains as host, with vectors containing DNA which encodes the promoter and signal peptides of extracellular enzyme gene or cell wall protein gene, for example of bacterial origin, α-amylases derived from *Bacillus licheniforis* [J. Bacteriol., 169, 1239(1987)] or derived from *Bacillus stearothermophilus* [Agric. Biol. Chem., 53, 2279 (1989)] and β-amylase derived from *Clostridium thermosulfurogenes* have been expressed at such production amounts of 0.5–3 g/L and 1.6 g/L, respectively.

Although many attempts to express proteins of eukaryote origin, from fungi to mammalians, in expression system of *Bacillus brevis* have been tried, human epithelial growth factor (EGF) of animal origin [Proc. Natl. Acad. Sci. USA, 86, 3589 (1989)], which consists of 53 amino acid sequences and has a relatively simple structure with small molecular size, is a solitary instance of high expression at such production amounts of 0.24–1.1 g/L. Taka-amylase A derived from *Aspergillus oryzae* [Journal of the Agricultural Chemical Society of Japan, 64, 728 (1990)], porcine pepsinogen [Appl. Microbiol. Biotechnol., 34, 297 (1990)], human salivary α-amylase (H. Konishi; Master Thesis in Nagoya University) and human interleukin-2 (Y. Takimura; Master Thesis in Nagoya University) of eukaryote origin have been also reported to be expressed in the *Bacillus brevis* expression system, the production amounts are very low, at such production amounts of 0.01–0.06 g/L. Moreover, physiologically-active proteins, such as antibodies, of mammalian origin with high molecular weights and complicated structures, have never been reported to be produced at high amounts in the *Bacillus brevis* expression system.

SUMMARY OF THE INVENTION

The present inventors investigated in search of a method of efficiently producing a functional recombinant antibody, and found that the desired antibody can be produced extracellularly in an active form in significant amounts in the culture by expressing the recombinant antibody gene using a bacterium of the genus Bacillus as host. The inventors made further investigations based on this finding, and developed the present invention.

Accordingly, the present invention relates to:

(1) A method for producing a functional recombinant antibody, comprising cultivating bacterium of the genus Bacillus transformed with a vector that contains DNA coding for an antibody under conditions suitable for expression of the functional antibody.

(2) The method of the above item (1) wherein the bacterium is *Bacillus brevis*.

(3) The method of the above item (1) wherein the antibody is produced in amounts of more than about 20 mg/L.

(4) The method of the above item (1) wherein the antibody is produced in amounts of more than about 50 mg/L.

(5) The method of the above item (1) wherein the antibody is Fab'.

(6) The method of the above item (1) wherein the antibody is selected from the group consisting of anti-enzyme antibody, anti-receptor antibody, anti-cytokine antibody, anti-hormone antibody, anti-adhesive protein antibody and anti-pathogenic substance antibody.

(7) The method of the above item (1) wherein the DNA contains a promoter region derived from a bacterium of the genus Bacillus.

(8) The method of the above item (1) wherein the antibody accumulates extracellularly.

(9) The method of the above item (1) wherein the antibody produced is purified to a purity of over 90 percent, based on protein weight.

(10) A DNA which comprises an antibody-encoding DNA linked to the 3'-terminal of DNA containing a promoter region capable of expression in a bacterium of the genus Bacillus.

(11) The DNA of the above item (10) wherein the bacteirum is *Bacillus brevis*.

(12) The DNA of the above item (10) wherein the antibody is Fab'.

(13) The DNA of the above item (10) wherein the promoter region is derived from a *Bacillus bacterium*.

(14) A vector which comprises the DNA of claim (10).

(15) A bacterium of the genus Bacillus which is transformed with the vector of the above item (14).

(16) The transformant of the above item (15) wherein the bacterium is *Bacillus brevis*.

BRIEF DESCRIPTION OF THE DRAWINGS

In the drawings, the symbols used therein are defined below:
Kbp: Kilobase pair
MWP: MWP promoter region
SP: MWP signal sequence
MCS: Multicloning site
Em: Erythromycin resistant gene coding region
VL: Light-chain variable region
CL: Light-chain constant region
VH: Heavy-chain variable region
CH: Heavy-chain constant region
h: Hinge region
SD: SD sequence

DETAILED DESCRIPTION OF THE INVENTION

The antibody mentioned herein refers to a protein produced in a living body by immune response to antigen stimulation and that specifically binds to an immunogen (antigen). Accordingly, the antibody may be any protein, as long as it is capable of specifically binding to an antigenic bioactive substance, such as a protein (e.g., enzyme, hormone, cytokine, receptor, adhesive protein, toxin, coagulation fibrinolysis factor), polysaccharide (e.g., cell wall polysaccharide), nucleic acid or lipid (e.g., lipid A, cardiolipin), or an assembly thereof (e.g., virion, pollen, house dust). The preferable antibody of this invention is the protein which is capable of specifically binding to an antigen of a pathogenic, substance or an etiological factor. More specifically, such antigens of pathogenic substance or etiological factors are proteinic ones and preferably include tumor-associated antigens, virions, bacterial toxins, receptors, adhesive proteins, cytokines, and so on. Such antibodies include anti-enzyme antibody, anti-receptor antibody, anti-cytokine antibody, anti-hormone antibody, anti-adhesive protein antibody., anti-pathogenic substance antibody and so on. The subject antibody may be of any size, ranging from whole molecules of 150,000 to 190,000 molecular weight to molecule fragments exceeding 20,000 to 24,000 molecular weight, which are active proteins of minimum size, based on the analysis by SDS-PAGE (SDS polyacrylamide gel electrophoresis). The molecular size of the antibody of this invention is preferably from 20,000 to 60,000, based on the analysis by SDS-PAGE (SDS polyacrylamide gel electrophoresis), more preferably 25,000 to 50,000.

The antibody may have natural or artificial mutations in the constituent amino acid sequence thereof, such as transfer, deletion, insertion and modification as long as it keeps bioactivities (e.g., ability of binding to antigen). More specifically, such antibodies include mouse antibodies, human antibodies, mouse/human chimeric antibodies, humanized antibodies, single-chain antibodies, single-domain antibodies, bispecific antibodies and toxin fusion antibodies. Also included are combinations of these antibodies, such as mouse/human chimeric bispecific antibodies, humanized bispecific antibodies and single-chain bispecific antibodies, exemplified by mouse/human chimeric anti-human fibrin (hereinafter abbreviated to FIB) specific antibodies, mouse/human chimeric anti-human urokinase (abbreviated to UK) antibodies and mouse/human chimeric anti-FIB/anti-UK bispecific antibodies [Japanese published unexamined patent application No. 76385/1993 (Kokai tokkyo koho hei No. 5-76385); European published unexamined patent application No. EP 0491351A]. Of the fragments constituting these antibodies, those capable of binding to antigens, such as fragments F(ab')$_2$, Fab', Fab, Fv and dab, particularly Fab', Fab and Fv, are preferable antibodies that can be obtained in an active form at high yields. Among these fragments, Fab' is more preferable antibody.

The subject DNA may be any one, as long as it encodes an antibody. DNA encoding an antibody is collected from, for example, genomic DNA or mRNA derived from a hybridoma that produces a monoclonal antibody (MoAb). Source hybridomas include mouse hybridomas UK1-3 (IFO No. 50176, FERM No. BP-2083) and FIB1-11 (IFO No. 50174, FERM No. BP-2081), which exhibit high specificity and affinity for human urokinase (UK) and fibrin, respectively. DNA or mRNA, derived from other several mouse hybridomas secreting mouse mono-clonal antibodies B72.3 [N. Whittle et al.: Protein Eng., 1, 499 (1987)], L6 [A. Y. Liu et al.: Proc. Natl. Acad. Sci. USA, 84, 3439 (1987)], 17-1A [L. K. Sun et al.: Proc. Natl. Acad. Sci. USA, 84, 214 (1987)], CEM231.6.7 [C. B. Beidler et al.: J. Immunol., 141, 4053 (1988)], MBrl [R. Orlandi et al.: Proc. Natl. Acad. Sci. USA, 86, 3833 (1989)] and SK3 [S. J. Knox et al.: Blood, 77, 20 (1991)] which specifically recognize TAG 72 (breast, ovarian and colorectal tumor-associated antigen), carcinoma and melanoma cells, gastrointestinal malignant cells, carcinoembryonic antigen (CEA), mammary carcinoma cells MCF-7 and CD4 antigen expressed on T cells, respectively, can also be used for the purpose of the present invention. It is possible, however, to use DNA or mRNA derived from a non-human mammal, such as the rabbit, goat, horse, bovine or rat, as long as it produces an antibody exhibiting sufficient specificity and affinity for subject antigen.

Genomic DNA for the present invention can be obtained and cloned by conventional known methods [Basic Methods in Molecular Biology, published by Elsevier, New York (1986); American Journal of Human Genetics, 37, 635 (1985)]. mRNA for the present invention can be prepared by ordinary methods, for use in preparing cDNA to clone [J. Sambrook et al., eds., Molecular Cloning/A Laboratory Manual, Cold Spring Harbor Laboratory Press, New York (1989)]. For example, hybridoma-derived genomic DNA is cleaved into fragments using restriction endonuclease, the resulting fragments are cloned to an appropriate DNA cloning vector; the desired clone is isolated via screening using a radio- or enzyme-labeled probe. Since the DNA from the genomic DNA usually contains intervening sequences not encoding polypeptides, it is modified into the DNA sequence having no intervening sequences by amino acid deletion or substitution by known methods [Nucleic Acids Research, 12, 9441 (1984); Proceedings of the National Academy of Science of the USA, 82, 488 (1985)].

Antibody-encoding DNA can also be obtained from a cDNA library by a known method [Molecular and Cellular Biology, 2, 161 (1982)]. The clones thus obtained may be screened for the desired clone using an appropriate probe; the cDNA can be treated in essentially the same procedure as for genomic DNA.

Antibody-encoding DNA can be efficiently prepared by a known method of specifically amplifying DNA, known as polymerase chain reaction (hereinafter abbreviated to PCR) [Proceedings of the National Academy of Science of the USA, 86, 3833 (1989)], or can be chemically synthesized by conventional methods [Nucleic Acids Research, 12, 4359 (1984)]. The synthetic DNA thus obtained, even if the original codon has been replaced by a degenerated codon, need not be identical with the DNA obtained by cloning, as long as it encodes the same amino acid upon translation. These DNAs can be obtained from hybridomas described above or they can be chemically synthesized according to the sequences determined using the hybridomas.

Any promoter can be used for the present invention, as long as it functions in a bacterium of the genus Bacillus. Promoters derived from *Bacillus brevis* are preferred, such as the promoter of the major extracellular protein gene of *Bacillus brevis* 47 (FERM P-7224) or *Bacillus brevis* H102 [FERM BP-1087, strain identical with *Bacillus brevis* HPD31 described by S. Udaka in Agric. Biol. Chem., 53, 691 (1989)]. One or more such promoters may be contained.

The DNA containing the promoter region must have an SD sequence, translation initiation codon etc., in addition to the promoter(s), and may contain parts of genes of major extracellular protein etc.

In the present invention, the antibody may accumulate in or outside the cells of a bacterium of the genus Bacillus. To facilitate antibody extraction and purification and increase productivity, it is preferable that the antibody be accumulated extracellularly in the culture supernatant. In such case, the DNA containing the promoter region includes on its 3'-terminal side a region encoding a signal peptide.

In the present invention, DNA sequence is constructed so as to code the signal peptide just before N terminal Sequence of the antibody. The signal peptide sequence is cut off, and the desired antibody can be prepared in a mature form, during the expression of the antibody in a bacterium of the genus Bacillus.

The signal peptide may be of any kind, as long as it causes secretory expression of the antibody outside the cells of a bacterium of the genus Bacillus. Such peptides include the signal peptide of the major extracellular protein of *Bacillus brevis* 47 or *Bacillus brevis* H102. The signal peptide of MW protein (middle wall protein, hereinafter also referred to as MWP) of *Bacillus brevis* 47 is preferred.

In the present invention, the vector contains DNA coding for an antibody under conditions suitable for expression of the functional antibody.

In the present invention, the antibody-encoding DNA can be used to be linked to the downstream, i.e. to the 3'-terminal of DNA containing said promoter region derived from a bacterium of the genus Bacillus. The expression of said antibody is under control of the promoter region.

Any expression vector can be used for the present invention, as long as it functions in a bacterium of the genus Bacillus. Such vectors include pHY500 and pNU200, both described in European published unexamined patent application No. EP-A-0326046.

The antibody expression vector prepared using the above-described DNA may be of any kind, as long as it functions in a bacterium of the genus Bacillus. Such vectors include vector pNU-Fab' as obtained in Example 1 below or pNU-Fab' (FIB).

These vectors can be constructed by, for example, the method described in T. Maniatis et al. Molecular Cloning/A Laboratory Manual (2nd ed. 1989).

Any host can be used to construct a vector, as long as it belongs to the species *Escherichia coil*, *Bacillus subtilis* or *Bacillus brevis*. Such microorganisms include *Escherichia coil* strains HB101 and DE1, *Bacillus subtilis* RM141 [Journal of Bacteriology, 158, 1054 (1984) ], *Bacillus brevis* 47 and *Bacillus brevis* 47-5 (FERM BP-1664, IFO 14698).

Although any host can be used for gene expression, as long as it is a bacterium of the genus Bacillus, *Bacillus brevis* is preferred. Example *Bacillus brevis* strains include *Bacillus brevis* 47, *Bacillus brevis* 47-5 and *Bacillus brevis* H102.

Each host bacterium is transformed with the above-mentioned vector that contains DNA coding for the desired antibody.

Known methods can be used to transform bacteria of the genus Bacillus, including the method of Takahashi et al. [Journal of Bacteriology, 156, 1130 (1983)], the method of Takagi et al. [Agricultural and Biological Chemistry, 53, 3099 (1989)] and the method of Udaka and Yamagata [Methods in Enzymology, 217, 23 (1983)]. For example, *Bacillus brevis* is serially transformed using two kinds of recombinant expression vectors, encoding the light and heavy chains of immunoglobulin Fab', respectively. Light- and heavy-chain expression vectors can be introduced into *Bacillus brevis* at the same, time. Alternatively, two DNA constructs encoding the light and heavy chains, respectively, may be connected to a single expression vector for transforming *Bacillus brevis*, to enable Fab' expression in one-time transformation.

Any medium can be used to culture the obtained transformant, as long as it allows the transformant to grow and produce the desired antibody at high yields.

Example carbon sources added to the medium include glucose, sucrose, glycerol, starch, dextrin, molasses, urea and organic acids. Example nitrogen sources added to the medium include organic nitrogen sources, such as casein, polypeptone, meat extract, yeast extract, casamino acid, amino acids (e.g., glycine) and NZ-amine, and inorganic nitrogen sources, such as ammonium sulfate, ammonium chloride and ammonium nitrate. In addition, inorganic salts, such as potassium chloride, monopotassium phosphate, dipotassium phosphate, sodium chloride and magnesium sulfate, are added, when necessary. A synthetic medium based on sugars and inorganic nitrogen sources may be used. When using an auxotroph, nutrients required for its growth are added to the medium. Such nutrients include amino acids, vitamins and nucleic acid bases. Antibiotics, such as penicillin, erythromycin, chloramphenicol and bacitracin, are added to the medium, when necessary. Antifoaming agents, such as soybean oil and lard, may be added to the medium.

Initial medium pH is normally 5 to 9, preferably 6.5 to 7.5.

Cultivating temperature is normally 15°–42° C., preferably 24°–37° C., cultivating time being normally 16–166 hours, preferably 24–96 hours.

After completion of culture, cells are separated from the supernatant by a known method, such as centrifugation or filtration. The intracellularly produced antibody is extracted by disrupting the cells by an ordinary method, such as ultrasonic disruption or French press disruption, with the addition of a surfactant, such as Triton X-100 or deoxycholic acid, as necessary. The thus-obtained antibody, contained in the culture supernatant or cell extract, is purified by ordinary protein purification methods, such as salting-out (ammonium sulfate or sodium sulfate used normally), gel filtration, ion exchange, hydroxyapatite, protein A, or antigen-binding affinity column chromatographies or high performance liquid chromatography (HPLC), to yield the desired antibody at high recovery. The present invention makes it possible to produce an antibody of over 90% purity, and typically more than 95%, including of from 95% to 100%, based on protein weight, at high yields of about 20 mg to 5 g per liter, typically about 50 mg to 2 g per liter, of culture supernatant. More particularly, the present invention enables expression of antibody in an active form at production amounts of more than about 20 mg/L of culture supernatant, and typically more than 50 mg/L, including of from about 50 mg/L to 5 g/L culture supernatant. Such expression production amounts will be achieved for a wide variety of antibodies, including e.g. mouse monoclonal anti-human fibrin antibody, mouse monoclonal anti-human urokinase antibody, mouse monoclonal anti-human fibrin/urokinase bispecific antibody, and their respective mouse/human chimeric antibodies.

The thus-obtained antibody can be quantified by radio-immunoassay (RIA), enzyme immunoassay (EIA) or HPLC. The binding activity of the antibody can also be determined using an antigen it recognizes. In the case of mouse/human chimeric anti-human UK antibody Fab', the sample solution is added to an immunoplate sensitized with human UK; the Fab' bound to the solid phase is detected using a goat anti-human IgG antibody labeled with horseradish peroxidase (HRP).

Although the antibody of the present invention can be used both in vitro and in vivo, mouse/human chimeric antibodies, humanized antibodies, human antibodies etc., in particular exhibit their function when administered to the human body, because they are low in immunogenicity. For example, administering the antibody of the present invention, as bound to an appropriate radioactive nuclide (e.g., $^{111}$In, $^{123}$I, $^{99m}$Tc) enables cancer or thrombosis imaging. The antibody of the present invention, when bound to an anticancer or thrombolytic substance, can be used to treat various cancers or thrombotic diseases such as myocardial infarction and cerebral infarction, respectively.

The antibody of the present invention can also be administered in the form of an injectable or other form of preparation, singly or in mixture with a pharmacologically acceptable carrier, excipient, diluent etc., after filtration and germ removal using a membrane filter. These preparations can be used to treat cancer, myocardial infarction, cerebral infarction, pulmonary embolism, allergies, inflammatory diseases and other diseases, and to prevent organ transplantation rejection.

Abbreviations for bases, amino acids, peptides and other entities used in the present specification and attached drawings are based on abbreviations specified by the IUPAC-IUB Commission on Biochemical Nomenclature (CBN) or abbreviations in common use in relevant fields. Some examples are given below. When an optical isomer may be present in amino acid etc., it is of the L-configuration, unless otherwise stated.

Unless otherwise stated, the left-to-right direction of an amino acid sequence is from amino terminus (N terminus) to carboxy terminus (C terminus), with "—" at both ends of the sequence representing a bond. In the case of a base sequence, the left-to-right direction is from 5' terminus to 3' terminus.

DNA: Deoxyribonucleic acid cDNA: Complementary deoxyribonucleic acid

RNA: Ribonucleic acid mRNA: Messenger RNA

A: 2'-deoxyadenylic acid residue

C: 2'-deoxycytidylic acid residue

G: 2'-deoxyguanidylic acid residue

T: Thymidylic acid residue

Cys: Cysteine

Pro: Proline

The present invention makes it possible to easily produce a desired recombinant antibody at low cost, in large amounts, as described below.

1) In the case of bacteria, such as *Escherichia coli*, a recombinant antibody is often intracellularly accumulated in the form of an inactive and water-insoluble inclusion body, and is difficult to recover in an active form, when expressed by conventional methods. The present invention enables the production of large amounts of antibody in an active form.

2) In the case of bacteria, such as *Escherichia coli*, extraction and purification of the expressed antibody takes large amounts of time and labor, because it is intracellularly accumulated. The present invention enables very easy purification of the desired antibody, because the protein is secreted extracellularly and produced in an active form. The present invention makes it possible to produce an antibody with more than 80% activity of the native one, and typically more than 85%, including of from about 85% to 100%.

3) Hybridoma cells, have been traditionally used to produce active antibodies, fail to offer other than antibody whole molecules of high molecular weight (e.g., mouse anti-human UK antibody, molecular weight about 155,000). The present invention makes it possible to produce an antibody in the form of a molecule of a less size necessary for active functioning (e.g., mouse/human chimeric anti-human UK antibody Fab', molecular weight about 48,000). This means that molar production of active protein has improved dramatically.

All documents mentioned herein are incorporated herein by reference in their entirety.

EXAMPLES

The present invention is hereinafter described in more detail by means of the following reference examples and examples, which are not to be construed as limiting the present invention. The present invention is characterized by the use of a bacterium of the genus Bacillus for successfully expressing the secretion of an antibody in an active form that is more complex in conformation than other proteins, and is not subject to limitation as to the kind of antibodies. In the examples below, recombinant DNA production and introduction into animal cells and microorganisms were performed in accordance with the following laboratory manuals, unless otherwise stated.

(1) T. Maniatis, E. F. Fritsch and J. Sambrook, eds., Molecular Cloning/A Laboratory Manual, 2nd ed. (1989), Cold Spring Harbor Laboratory (USA).

(2) Y. Takagi, ed., Idenshi Sosa Jikkenho, 6th print (1985), Kodansha Ltd.

The animal cell lines and microorganisms used in the following reference examples and examples have been deposited as follows:

| Animal Cell Line/ Microorganism | IFO Number | FERM Number (NIBH) |
|---|---|---|
| Mouse hybridoma UK1-3 | 50176 (September 21, 1988) | BP-2083 (October 4, 1988) |
| Mouse hybridoma FIB1-11 | 50174 (September 21, 1988) | BP-2081 (October 4, 1988) |
| Mouse myeloma FIB1-H01/x63 | 50257 (October 17, 1990) | BP-3141 (October 25, 1990) |
| Bacillus brevis 47-5 | 14698 (January 12, 1988) | BP-1664 (January 20, 1988) |
| Bacillus brevis 47-5/pHY500-EGF | 14699 (January 12, 1988) | BP-1663 (January 20, 1988) |
| Bacillus brevis H102 | | BP-1087 (June 24, 1986) |
| Bacillus brevis 47K | | BP-2308 (February 28, 1989) |
| Bacillus brevis OK | | BP-4573 (November 11, 1992) |
| Bacillus brevis 47-5/pNU200-EGF | 14728 (February 19, 1988) | BP-1771 (February 29, 1988) |
| Bacillus brevis 47-5/pNU200-EGF31 | 14729 (February 19, 1988) | BP-1772 (February 29, 1988) |
| Bacillus brevis HPD31-OK/pNU-Fab' | 15651 (February 7, 1994) | BP-4567 (February 14, 1994) |
| Bacillus brevis 47K/pNU-Fab' | 15650 (February 7, 1994) | BP-4566 (February 14, 1994) |

IFO: Institute for Fermentation, Osaka (foundation)
NIBH: National Institute of Bioscience and Human-Technology, Agency of Industrial Science and Technology, Ministry of International Trade and Industry

*Bacillus brevis* OK (deposited under the assertion number P-13274 on Nov. 11, 1992 and this deposition has been changed to international deposition under the assertion number BP-4573 on February 17, 1994.

Example 1

Construction of Antibody Expression Vector pNU-Fab'

Figure 1:
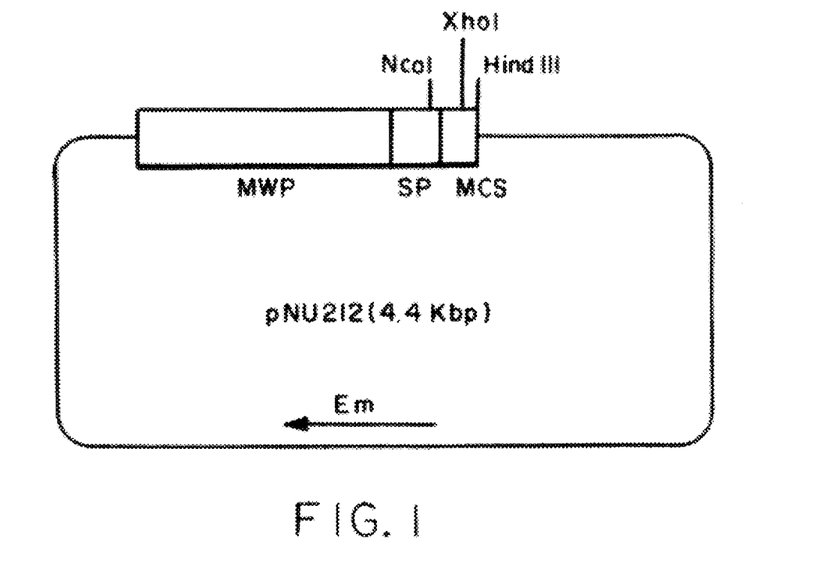
FIG. 1 shows the structure of the MW protein secretory expression vector (pNU212) described in Example 1.
Figure 2:
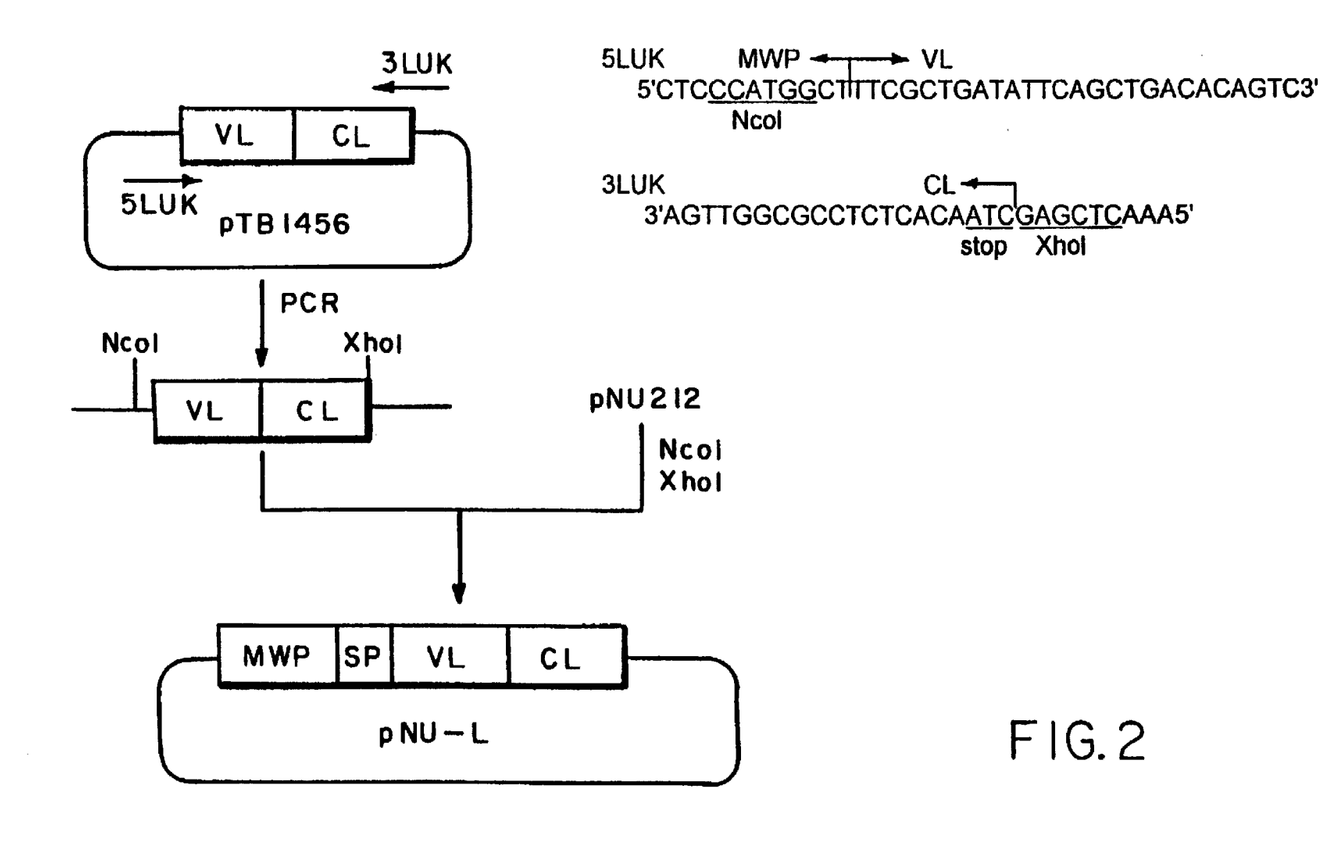
FIG. 2 shows the structure of the anti-human urokinase antibody light chain secretory expression vector (pNU-L) constructed in Example 1 and the PCR primers (SEQ ID NOS:1 and 2) used to amplify the desired sequence.
Figure 3:
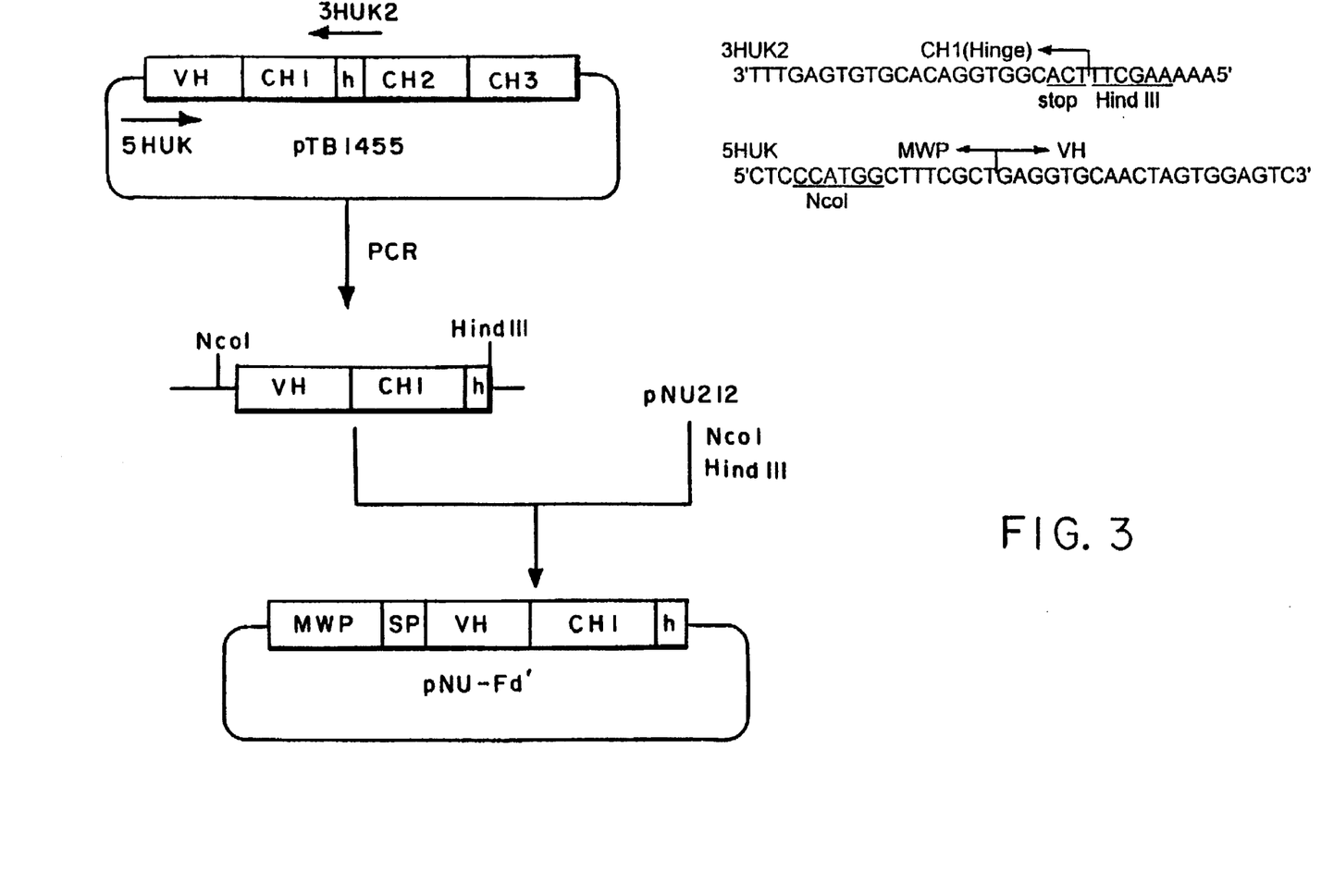
FIG. 3 shows the structure of the anti-human urokinase antibody Fd' chain secretory expression vector (pNU-Fd') constructed in Example 1 and the PCR primers (SEQ ID NOS:3 and 4) used to amplify the desired sequence.
Figure 4:
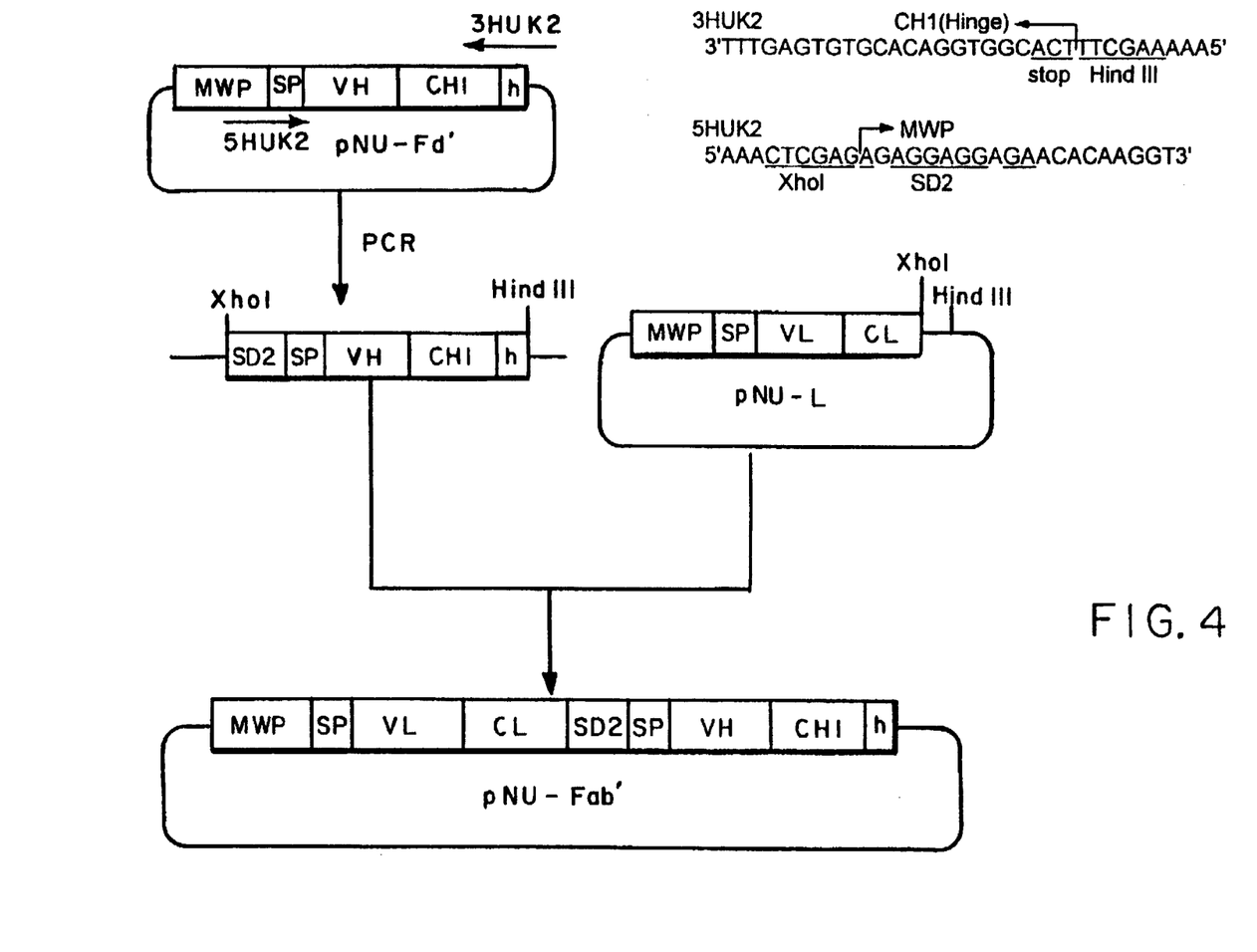
FIG. 4 shows the structure of the anti-human urokinase antibody Fab' chain secretory expression vector (pNU-Fab') constructed in Example 1 and the PCR primers (SEQ ID NOS:4 and 5) used to amplify the desired sequence.

Using pTB1456 as obtained in accordance with Example 5 (2) of European published unexamined patent application No. EP 0491351A, as a template, and synthetic oligonucleotides 5LUK (SEQ ID NO:1) and 3LUK (SEQ ID NO:2), as primers, PCR was performed; the resulting fragment was digested with NcoI-XhoI to yield a DNA fragment encoding an antibody light chain. Separately, to an about 4.3 kb fragment obtained by digesting pNU212 shown in FIG. 1 [essentially identical with pNU210 described in Methods in Enzymology, 217, 23 (1993)] with NcoI-XhoI, the above light chain encoding fragment was ligated, to yield pNU-L. The construction scheme is shown in FIG. 2. Next, using pTB1455, obtained in accordance with Example 5 (3) of European published unexamined patent application No. EP 0491351A, as a template, and synthetic oligonucleotides 5HUK (SEQ ID NO:3) and 3HUK2 (SEQ ID NO:4), as primers, PCR was performed. 3HUK2 (SEQ ID NO:4) is designed to have a termination codon introduced just after Cys-Pro-Pro into a portion encoding the C-terminal Cys-Pro-Pro-Cys-Pro in the antibody hinge region. The resulting DNA fragment was digested with NcoI-HindIII to yield a DNA fragment encoding the Fd' fragment. This fragment was ligated to an about 4.3 kb fragment, obtained by digesting pNU212 with NcoI-HindIII, to yield pNU-Fd'. The construction scheme is shown in FIG. 3. Next, using pNU-Fd' as a template, and synthetic oligonucleotides 5HUK2 (SEQ ID NO:5) and 3HUK2 (SEQ ID NO:4), as primers, PCR was performed. The resulting fragment was digested with XhoI-HindIII to yield a DNA fragment encoding the SD sequence through the H-chain hinge region of the MWP promoter. This fragment was ligated to an about 5 kb fragment obtained by digesting pNU-L with XhoI-HindIII, to yield Fab' fragment secretory expression vector pNU-Fab'. The construction scheme is shown in FIG. 4.

The thus-obtained pNu-Fab' vector was digested using various restriction enzymes; it was identified as the desired vector. Also, the PCR-amplified region proved to have the correct base sequence, as confirmed by a known method of dideoxy chain termination.

Example 2

Antibody Gene Expression in *Bacillus brevis*

*Bacillus brevis* strains OK (FERM P-13274, BP-4573) and 47K (FERM BP-2308) [Konishi et al., Applied Microbiology and Biotechnology, 34, 297 (1990)] were used as hosts; these strains of low extracellular protease activity were obtained via various mutating treatments by known methods, from known bacteria of the genus Bacillus, namely *Bacillus brevis* H102 (FERM BP-1087, strain identical with *Bacillus brevis* HPD31) and *Bacillus brevis* 47 (FERM P-7224), respectively. Using vector pNU-Fab' as obtained in Example 1, *Bacillus brevis* strain which belongs to the groups of strains HPD31 or 47 was transformed as follows.

(1) The strain which belongs to the group of strain HPD31 was transformed by a known method of electropotation [Agricultural and Biological Chemistry, 53, 3099 (1989), under conditions of 1.5 kV, 25 µF and 1,000 Ω, using a 0.2 cm cuvette, with a 7 mM sodium phosphate buffer (pH 7.4) containing 2.33% sucrose, 10 mM $MgCl_2$ and 15% glycerol, as transforming solution.

(2) The strain which belongs to the group of strain 47 was transformed by another known method [Methods in Enzymology, 217, 23 (1993)]. Specifically, the strain was subjected to overnight shaking culture at 37° C. in 5 ml of T2u medium of the composition shown below, to yield a preculture which was transferred to 100 ml of T2u medium and cultivated at 37° C. for 4 to 5 hours. When culture absorbance at 660 nm reached 3.5 to 4.0 (growth rate began to decrease slightly), the culture was kept in ice for 30 minutes, after which cells were harvested and washed by sequential additions of 200 ml, 100 ml and 4 ml of a 0.1 mM phosphate buffer (pH 7.4) containing 9.32% sucrose and 15% glycerol (hereinafter also referred to as solution A). The cells were then suspended in 0.5 ml of solution A; the suspension was dispensed to centrifugal tubes at 45 µl per tube, and stored at −80° C. under freezing conditions in dry ice/ethanol mixture. To 45 µl of this competent cell suspension, 1 to 2 µl of DNA solution was added; the mixture was pulsated using a 0.1 cm cuvette and gene pulsar (produced by Bio-Rad Laboratories) at 0.9 kV, 25 µF and 200 Ω. 1 ml of T2u medium containing 20 mM $MgCl_2$, previously cooled, was immediately added. After being kept in ice for 10 minutes, the mixture was subjected to shaking culture at 30° C. for 1 hour; erythromycin was added to yield a final concentration of 0.1 µg/ml. After 4 more hours of shaking culture at 30° C., the culture was applied to T2u solid medium containing 10 µg/ml erythromycin, and subjected to standing culture at 30° C.

*Bacillus brevis* strains OK and 47K were thus transformed into *Bacillus brevis* HPD31-OK/pNU-Fab' (IFO 15651) and *Bacillus brevis* 47K/pNU-Fab' (IFO 15650), both strains encoding the antibody Fab'.

T2u medium: 1% polypeptone, 0.5% meat extract, 0.2% yeast extract, 0.1 mg/ml uracil and 1% glucose

Example 3

Characterization of Expressed Antibody Fab' (I)

(1) Cultivation of the Transformant

*Bacillus brevis* strain HPD31-OK/pNU-Fab' as obtained in Example 2 was cultivated in 2PY medium at 30° C. One day later, glucose was added to a final concentration of 5%, followed by 2 more days of cultivating. The resulting culture was electrophoresed on 12% SDS polyacrylamide gel and assayed by Western blotting [T. Maniatis, E. F. Fritsch, J. Sambrook, eds., Molecular Cloning, Cold Spring Harbor Laboratory, USA]. HRP-labeled goat anti-human $F(ab')_2$ antibody F(ab')2 (produced by Kappel) was used as a detection probe; the standard preparation used was the human IgG.Fab produced by Protogen.

The culture liquid proved to contain the antibody Fab' at high concentrations exceeding 0.5 g/l.

2PY medium: 4% proteose peptone, 0.5% yeast extract, 2% glucose, 0.01% $MgSO_4.7H_2O$, 0.001% $FeSO_4.7H_2O$, 0.001% $MnSO_4.4H_2O$, 0.0001% $ZnSO_4.7H_2O$ (pH 7.0)

(2) Purification of the Antibody Fab'

*Bacillus brevis* strain 47K/pNU-Fab' as obtained in Example 2 was cultivated at 30° C. in 2PY medium containing 0.1 mg/ml uracil. One day later, glucose was added to yield a final concentration of 5%, followed by 2 more days of culture, subpart (1) above of this Example 3. The resulting culture was subjected to salting-out using ammonium sulfate 40–60% saturation fractions. The resulting precipitate was dialyzed against 20 mM Tris-HCl buffer (pH 7.5).

Next, the culture was subjected to ion exchange column chromatography using DE52 (produced by Whatman K. K.); the effluent eluted with 20 mM Tris-HCl buffer (pH 7.5) was collected (elution rate, 39 ml/hr). After salting-out using an ammonium sulfate 60% saturation fraction, the effluent fraction was dialyzed against 20 mM Tris-HCl buffer (pH 7.5).

Next, the dialyzate was subjected to gel filtration chromatography using a Sephadex G-75 column (produced by Pharmacia) (eluent, 10 mM Tris-HCl buffer, pH 7.5, containing 0.1M NaCl; elution rate, 10 ml/hr), and was then purified by protein G affinity chromatography using an MAb Trap G II kit (produced by Pharmacia).

(3) Physico-Chemical Property of the Antibody Fab'

The obtained purified antibody Fab' solution was subjected to electrophoresis on 12% SDS polyacrylamide gel under reducing and non-reducing conditions; the antibody was detected via coumassie brilliant blue staining. Under non-reducing conditions, a clear band appeared at a position corresponding to a molecular weight of about 48,000, demonstrating the presence of antibody Fab'. Under reducing conditions, two bands appeared at around a molecular weight of about 28,000, demonstrating antibody Fab' dissociation into two single chains: L and Fd' chains.

Next, the above two bands were analyzed for N-terminal amino acid sequence; the correct sequence was found between N-terminus and 10th amino acid residue; the band on the higher molecular side proved to be the L chain, that on the lower molecular side the Fd' chain. At the same time, signal peptide cleavage at the correct position was confirmed.

(4) Antigen Affinity of Antibody Fab'

30 µg of human urokinase (produced by Protogen) was dissolved in water; the solution was adjusted to pH 4.5. Separately, 2 mg of N-ethyl-N'-(3,3'-dimethyl-aminopropyl) carbodiimide hydrochloride was similarly dissolved in water; the solution was adjusted to pH 4.5. Both aqueous solutions were added to EAH-Sepharose 4B suspension (produced by Pharmacia), followed by overnight shaking at room temperature to cause reaction. After thorough water-washing, the reaction mixture was packed in a column and equilibrated with 10 mM Tris-HCl buffer 7.5).

A purified antibody Fab' solution, subpart (3) above of this Example 3, was applied to the above urokinase-coupled column and thoroughly washed with the equilibrating buffer. Solution pH was then decreased step by step in 0.5 unit decrements, using 50 mM glycine-HCl buffer; the recovered eluate was subjected to SDS polyacrylamide gel electrophoresis to detect the antibody Fab' via silver staining.

In the case of eluates with pH up to 3.0, the antibody Fab' was not eluted from the column; the antibody Fab' was first detected from the pH 2.5 eluate. For control, the same experiment was conducted using a human IgG/Fab fraction (produced by Protogen); the fraction was mostly detected in eluates with pH under 3.0.

These findings demonstrate that the antibody Fab' as prepared according to the present invention exhibits strong binding affinity to the antigen human urokinase.

Example 4

Characterization of Expressed Antibody Fab' (II)

(1) Cultivation of the Transformant

*Bacillus brevis* strain HPD31-OK/pNU-Fab' as obtained in Example 2 was cultivated at 30° C. in 5PY medium containing 10 µg/ml of erythromycin. One day later, glucose was added to a final concentration of 3%, followed by 2 more days of cultivating. The production amount of Fab' was determined by Western blotting as shown in Example 3-(1), and found to be more than approximately 50 mg/L.

5PY medium: 4% proteose peptone, 0.5% yeast extract, 2% glucose, 0.01% $MgSO_4 \cdot 7H_2O$, 0.001% $FeSO_4 \cdot 7H_2O$, 0.001% $MnSO_4 \cdot 4H_2O$, 0.0001% $ZnSO_4 \cdot 7H_2O$, 2 mM $CaCl_2 \cdot 2H_2O$ (pH 7.0).

(2) Purification of the Antibody Fab'

The culture supernatant 560 ml was recovered by centrifugation, followed by purification procedures for the antibody Fab', as described below. (i) The supernatant was subjected to salting-out using ammonium sulfate 40–60% saturation, and the resulting precipitate was dialyzed against 20 mM Tris-HCl buffer (pH 7.5). (ii) The antibody-containing solution was subjected to a DEAE-cellulose column (Whatman DE52). (iii) The passed-through fraction was concentrated by salting-out using ammonium sulfate 80% saturation, and the resulting precipitate was dialyzed against 20 mM Tris-HCl buffer (pH 7.5). (iv) The antibody-containing solution was subjected to a Mono Q column (produced by Pharmacia) and separated with a gradient elution using 0–500 mM NaCl. Fab' was eluted with approximately 100 mM NaCl. (v) After addition of 1M phosphate buffer (pH 6.8) to give a final concentration of 10 mM, the Fab'-containing fraction was subjected to a hydroxyapatite column. (vi) The passed-through fraction was dialyzed against 10 mM phosphate buffer (pH 6.8) to remove NaCl. (vii) The antibody-containing solution was subjected to a hydroxyapatite column in the absence of NaCl and separated with a gradient elution using 10–200 mM NaCl-containing 10 mM phosphate buffer (pH 6.8). Fab' was eluted with approximately 50 mM NaCl.

Approximately 6 mg of Fab' was obtained by the procedures described above.

(3) Property of the Antibody Fab'

Figure 5:
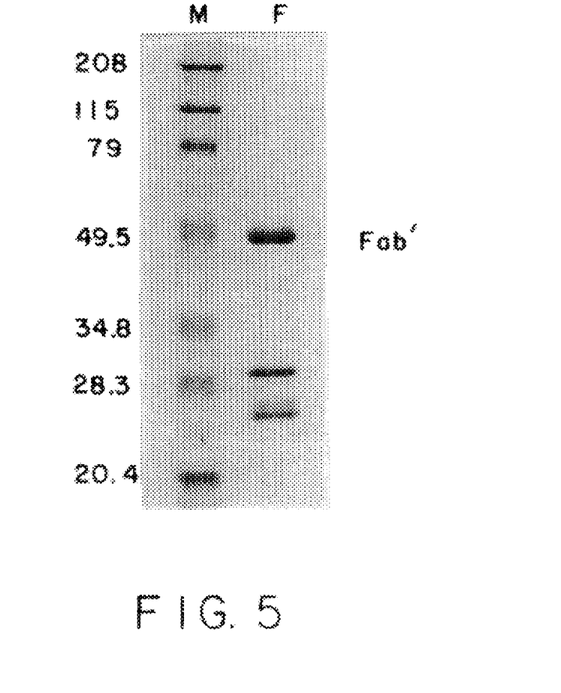
FIG. 5 shows the SDS polyacrylamide gel electrophoretic patterns of the purified anti-human urokinase antibody Fab' obtained in Example 4, under non-reducing condition [M represents molecular weight markers (208, 115, 79, 49.5, 34.8, 28.3, 20.4 K) and F represents 2 µg of Fab'].

The obtained purified antibody Fab' was subjected to SDS polyacrylamide gel electrophoresis under non-reducing condition, as described in Example 3-(3). The electrophoretic patterns are shown in FIG. 5.

A clear main band was detected at a position corresponding to a molecular weight of about 48,000. Two faint bands appeared at around molecular weights of about 25,000 and 30,000, which probably correspond to non-associating L and Fd' chains, respectively.

(4) Binding Constant to Human Urokinase

The obtained purified antibody Fab' was subjected to the enzyme immunoassay reported by Katoh et al. [J.Ferment.Bioeng., 76, 451 (1993)] and compared in binding constant to antigen with the original mouse monoclonal anti-human urokinase antibody UK1-3. The assay was performed using ABTS [2,2'-azino-bis(3-ethylbenzothiazoline-6-sulfonic acid)diammonium salt] as a color-developing agent and a microplate reader purchased from Bio-Rad (Model 450) for the measurement of the absorbance at 405 nm.

The purified antibody Fab' of the present invention gave a binding constant of $1.9 \times 10^8 M^{-1}$, which was comparable to that ($2.7 \times 10^8 M^{-1}$) of mouse monoclonal antibody UK1-3 obtained by the cell culture of the mouse hybridoma. These results demonstrated that the mouse-human chimeric anti-human urokinase antibody Fab' was expressed in and secreted from Bacillus brevis in active form with normal antigen-binding ability.

Example 5

Construction of Antibody Expression Vector pNU-Fab'(FIB)

Using pTB1423 and pTB1420 [J.Biotechnol., 33, 157–174 (1994)] instead of pTB1456 and pTB1455, pNU-L(FIB) and pNU-Fd'(FIB) are constructed as obtained in Example 1. Next, using pNU-L(FIB) and pNU-Fd'(FIB), pNU-Fab'(FIB) is yielded as an expression vector for secretion of anti-human fibrin-specific antibody Fab' fragment in the same manner as described in Example 1.

Example 6

Anti-Human Fibrin-Specific Antibody Gene Expression in *Bacillus brevis*

*Bacillus brevis* strain OK is transformed by electroporation [Agr.Biol.Chem., 53, 3099 (1989)] with pNU-Fab'(FIB) obtained in Example 5.

Thus obtained *Bacillus brevis* strain HPD31-OK/pNU-Fab'(FIB), is cultivated in 2PY medium at 30° C. One day later, glucose is added to final concentration of 5%, followed by 2 more days of cultivating. The resulting culture is assayed by Western blotting using 12% SDS polyacrylamide gel as described in Example 3. The culture fluid proves to contain the Fab' fragment of antibody against human fibrin at high concentrations exceeding 0.5 g/L.

The culture fluid is subjected to salting-out using 50% saturated ammonium sulfate. After dialysis against phosphate-buffered saline (pH 7.3), the antibody-containing solution is applied to a fibrin-coupled cellulofine column [Bio/Technol., 7, 1163 (1989)], followed by a hydroxyapatite high-performance liquid chromatography column (purchased from Mitsui Toatsu Chem.).

Purified Fab' fragment thus obtained is subjected to electrophoresis on 12% SDS polyacrylamide gel under reducing conditions as described in Example 3. Two bands appear at molecular weights ranging from 25,000 to 30,000, demonstrating Fab' dissociation into L and Fd' chains.

As for the affinity of the purified Fab' fragment to human fibrin, the enzyme immunoassay described in Example 4-(4) can be performed using fibrin monomer-coated microplates [Bio/Technol., 7, 1163 (1989)] instead of human urokinase-coated microplates. The purified antibody Fab' against human fibrin of the present invention proves to give a high binding constant comparable to that of mouse monoclonal antibody FIB1-11 obtained by the cell culture.

What is claimed is:

1. A method for producing a functional recombinant antibody, comprising cultivating *Bacillus brevis* bacterium transformed with a vector that contains DNA coding for an antibody under conditions wherein functional recombinant antibody is produced.

2. The method of claim 1 wherein the bacterium is selected from the group consisting of *Bacillus brevis* 47; *Bacillus brevis* 47-5; *Bacillus brevis* 47-5/pHY500-EGF; *Bacillus brevis* 47K; *Bacillus brevis* 47-5/pNU200-EGF; *Bacillus brevis* 47-5/pNU200-EGF31; *Bacillus brevis* 47K/pNU-Fab'; *Bacillus brevis* H102; *Bacillus brevis* OK; *Bacillus brevis* HPD31; and *Bacillus brevis* HPD31-OK/pNU-Fab'.

3. The method of claim 1 wherein the antibody is produced in amounts of more than about 20 mg/L.

4. The method of claim 1 wherein the antibody is produced in amounts of more than about 50 mg/L.

5. The method of claim 1 wherein the antibody is Fab'.

6. The method of claim 1 wherein the antibody is selected from the group consisting of anti-enzyme antibody, anti-receptor antibody, anti-cytokine antibody, anti-hormone antibody, anti-adhesive protein antibody and anti-pathogenic substance antibody.

7. The method of claim 1 wherein the DNA contains a promoter region derived from a bacterium of the genus Bacillus.

8. The method of claim 1 wherein the antibody accumulates extracellularly.

9. The method of claim 1 wherein the antibody produced is purified to a purity of over 90 percent, based on protein weight.

10. The method of claim 1 wherein the bacterium is selected from the group consisting of *Bacillus brevis* 47K and *Bacillus brevis* OK.

11. A DNA which comprises an antibody-encoding DNA linked to the 3'-terminus of DNA containing a promoter region which functions in a *Bacillus brevis* bacterium.

12. The DNA of claim 11 wherein the bacterium is selected from the group consisting of *Bacillus brevis* 47; *Bacillus brevis* 47-5; *Bacillus brevis* 47-5/pHY500-EGF; *Bacillus brevis* 47K; *Bacillus brevis* 47-5/pNU200-EGF; *Bacillus brevis* 47-5/pNU200-EGF31; *Bacillus brevis* 47K/pNU-Fab'; *Bacillus brevis* H102; *Bacillus brevis* OK; *Bacillus brevis* HPD31; and *Bacillus brevis* HPD31-OK/pNU-Fab'.

13. The DNA of claim 11 wherein the antibody is Fab'.

14. The DNA of claim 11 wherein the promoter region is derived from a Bacillus bacterium.

15. A vector which comprises the DNA of claim 11.

16. A *Bacillus brevis* bacterium which is transformed with the vector of claim 15.

17. The bacterium of claim 16 wherein the bacterium is selected from the group consisting of *Bacillus brevis* 47; Bacillus 47-5; *Bacillus brevis* 47-5/pHY500-EGF; *Bacillus brevis* 47K; *Bacillus brevis* 47-5/pNU200-EGF; *Bacillus brevis* 47-5/pNU200-EGF31; *Bacillus brevis* 47K/pNU-Fab'; *Bacillus brevis* H102; *Bacillus brevis* OK; *Bacillus brevis* HPD31; and *Bacillus brevis* HPD31-OK/pNU-Fab'.

* * * * *

UNITED STATES PATENT AND TRADEMARK OFFICE
CERTIFICATE OF CORRECTION

PATENT NO.    : 5,665,570
DATED         : September 9, 1997
INVENTOR(S)   : H. Yamagata et al.

It is certified that error appears in the above-identified patent and that said Letters Patent is hereby corrected as shown below:

<u>Title page,</u>
After "[73] Assignee: Takeda Chemical Industries, Ltd., Osaka, Japan" please insert -- Shigezo Udaka, Aichi, Japan --.

Signed and Sealed this

Thirtieth Day of July, 2002

Attest:

Attesting Officer

JAMES E. ROGAN
*Director of the United States Patent and Trademark Office*